(12) United States Patent
Migita et al.

(10) Patent No.: US 8,942,453 B2
(45) Date of Patent: Jan. 27, 2015

(54) ULTRASONOGRAPH AND METHOD OF DIAGNOSIS USING SAME

(75) Inventors: Manabu Migita, Kanagawa (JP); Yoshihiko Itoh, Kanagawa (JP); Akihiro Kawabata, Kanagawa (JP); Takehiko Suginouchi, Kanagawa (JP); Makiko Urabe, Tokyo (JP); Yushi Nishimura, Tokyo (JP)

(73) Assignee: Konica Minolta, Inc., Tokyo (JP)

( * ) Notice: Subject to any disclaimer, the term of this patent is extended or adjusted under 35 U.S.C. 154(b) by 455 days.

(21) Appl. No.: 13/496,579

(22) PCT Filed: Sep. 21, 2010

(86) PCT No.: PCT/JP2010/005708
§ 371 (c)(1),
(2), (4) Date: Mar. 16, 2012

(87) PCT Pub. No.: WO2011/033793
PCT Pub. Date: Mar. 24, 2011

(65) Prior Publication Data
US 2012/0177276 A1        Jul. 12, 2012

(30) Foreign Application Priority Data

Sep. 18, 2009    (JP) .................. 2009-216662

(51) Int. Cl.
*G06K 9/00*      (2006.01)
*A61B 8/00*      (2006.01)
(Continued)

(52) U.S. Cl.
CPC ... *A61B 8/42* (2013.01); *A61B 8/06* (2013.01); *A61B 8/0891* (2013.01); *A61B 8/4281* (2013.01); *A61B 8/463* (2013.01); *A61B 8/4245* (2013.01); *A61B 8/464* (2013.01)
USPC ........... 382/131; 382/100; 382/103; 382/128; 600/443; 600/444; 600/446; 600/447

(58) Field of Classification Search
None
See application file for complete search history.

(56) References Cited

U.S. PATENT DOCUMENTS

| 5,558,091 A | 9/1996 | Acker et al. |
| 5,833,608 A | 11/1998 | Acker |

(Continued)

FOREIGN PATENT DOCUMENTS

| CN | 1132470 A | 10/1996 |
| JP | 2003245280 A | 9/2003 |

(Continued)

OTHER PUBLICATIONS

International Preliminary Report on Patentability issued Apr. 19, 2012 in International (PCT) Application No. PCT/JP2010/005708.
(Continued)

*Primary Examiner* — Matthew Bella
*Assistant Examiner* — Jason Heidemann
(74) *Attorney, Agent, or Firm* — Holtz, Holtz, Goodman & Chick PC

(57) ABSTRACT

An ultrasonograph of the present invention comprises a probe (1), a controller (3) connected to the probe (1), and a display (4) connected to the controller (3). The controller (4) causes the display (4) to display a detected image of a target object detected by the probe (1) and an angular position relationship image showing a relative angular position of the probe to the detected image of the target object. This enables even a non-expert to take accurate measurements.

7 Claims, 16 Drawing Sheets

(51) Int. Cl.
*A61B 8/06* (2006.01)
*A61B 8/08* (2006.01)

(56) References Cited

U.S. PATENT DOCUMENTS

| | | | |
|---|---|---|---|
| 6,427,314 | B1 | 8/2002 | Acker |
| 6,623,431 | B1 | 9/2003 | Sakuma et al. |
| 6,669,641 | B2 * | 12/2003 | Poland et al. ............... 600/447 |
| 6,709,394 | B2 * | 3/2004 | Frisa et al. ................. 600/445 |
| 6,755,788 | B2 * | 6/2004 | Demers et al. ............. 600/447 |
| 6,761,689 | B2 * | 7/2004 | Salgo et al. ................ 600/447 |
| 7,500,952 | B1 * | 3/2009 | Chiang et al. .............. 600/446 |
| 7,925,327 | B2 | 4/2011 | Weese |
| 2003/0023166 | A1 * | 1/2003 | Frisa et al. ................. 600/443 |
| 2003/0060710 | A1 * | 3/2003 | Salgo et al. ................ 600/443 |
| 2003/0097067 | A1 * | 5/2003 | Poland et al. .............. 600/443 |
| 2003/0195421 | A1 * | 10/2003 | Demers et al. ............. 600/437 |
| 2006/0176242 | A1 * | 8/2006 | Jaramaz et al. ................. 345/7 |
| 2006/0262961 | A1 * | 11/2006 | Holsing et al. ............. 382/103 |
| 2007/0021738 | A1 * | 1/2007 | Hasser et al. .................... 606/1 |
| 2008/0021322 | A1 * | 1/2008 | Stone et al. ................ 600/443 |
| 2008/0287805 | A1 * | 11/2008 | Li ............................... 600/471 |
| 2010/0022871 | A1 * | 1/2010 | De Beni et al. ............ 600/424 |
| 2010/0185090 | A1 | 7/2010 | Suzuki et al. |
| 2010/0210946 | A1 | 8/2010 | Harada et al. |
| 2010/0222680 | A1 * | 9/2010 | Hamada ...................... 600/443 |
| 2010/0298704 | A1 * | 11/2010 | Pelissier et al. ............ 600/443 |
| 2011/0246129 | A1 | 10/2011 | Ishikawa et al. |

FOREIGN PATENT DOCUMENTS

| | | |
|---|---|---|
| JP | 2006508731 A | 3/2006 |
| JP | 2007090049 A | 4/2007 |
| JP | 2009-56125 | 3/2009 |
| JP | 2009-89911 | 4/2009 |
| JP | 2009089736 A | 4/2009 |
| WO | 2004051579 A2 | 6/2004 |
| WO | 2009013871 A1 | 1/2009 |

OTHER PUBLICATIONS

International Search Report issued Dec. 7, 2010 in International (PCT) Application No. PCT/JP2010/005708.

James H. Stein et al., "Use of Carotid Ultrasound to Identify Subclinical Vascular Disease and Evaluate Cardiovascular Disease Risk: A Consensus Statement from the American Society of Echocardiography Carotid Intima-Media Thickness Task Force Endorsed by the Society for Vascular Medicine", Journal of the American Society of Echocardiography, Feb. 2008 (pp. 93 to 111).

Chinese Office Action dated Nov. 25, 2013 issued in counterpart Chinese Application No. 201080043691.3.

Japanese Office Action dated Jun. 3, 2014 issued in counterpart Japanese Application No. 2011-507479.

Japanese Office Action dated Mar. 4, 2014 issued in counterpart Japanese Application No. 2011-507479.

* cited by examiner

ULTRASONOGRAPH AND METHOD OF DIAGNOSIS USING SAME

TECHNICAL FIELD

The present invention relates to an ultrasonograph and a method of diagnosis using the same.

BACKGROUND ART

Recently, an ultrasonograph has drawn attention as, for example, an instrument for determining a carotid condition, and has been know as being configured as described below.

For example, a conventional ultrasonograph comprises a probe, a controller connected to the probe, and a display connected to the controller. In the conventional ultrasonograph, a detected image of a target object (carotid artery) detected by the probe is displayed on the display (for example, see Non Patent Literature 1).

With the conventional ultrasonograph, however, it has been difficult for a person who is not a fully trained expert to take accurate measurements in determining a condition of a target object, or a carotid artery.

In this respect, when the conventional ultrasonograph is used to determine a carotid condition, the probe must be applied to a position bisecting a carotid artery longitudinally along the center line. However, different individuals have different locations and shapes of carotid arteries and the carotid arteries are not visible from the surface of the body.

Therefore, only a fully trained expert has been able to apply the probe accurately to a position bisecting a carotid artery longitudinally along the center line, and as a result, it has been difficult to take accurate measurements.

CITATION LIST

Non Patent Literature

Non Patent Literature 1: Journal of the American Society of Echocardiography February 2008 (p.p. 93 to 111)

SUMMARY OF INVENTION

Technical Problem

The present invention has been made under such circumstances. It is an object of the invention to provide an ultrasonograph and a method of diagnosis that enable even a non-expert to easily position a probe on the center line of a carotid artery so as to take accurate measurements.

Solution to Problem

One aspect of the invention is an ultrasonograph. The ultrasonograph comprises a controller to which a probe and a display are connected, wherein the controller causes the display to display a detected image of a target object detected by the probe and an angular position relationship image showing a relative angular position of the probe to the detected image of the target object.

As described below, the present invention has other aspects. Therefore, the disclosure of the invention is intended to provide some of the aspects of the invention, and is not intended to limit the scope of the invention as described and claimed herein.

BRIEF DESCRIPTION OF DRAWINGS

FIG. 4(a) is a diagram for illustrating a target object (region A) of the carotid artery; FIG. 4(b) is a cross-sectional view taken at a plane perpendicular to the center line of the carotid artery and is for illustrating the membrane arrangement; FIG. 4(c) is a cross-sectional view taken at a plane perpendicular to the center line of the carotid artery and is for illustrating a plaque; FIG. 4(d) is a cross-sectional view taken at a plane including the center axis of the carotid artery and shows no particular condition; FIG. 4(e) is a cross-sectional view taken at a plane including the center axis of the carotid artery and shows a condition where careful watching is needed; and FIG. 4(f) is a cross-sectional view taken at a plane including the center axis of the carotid artery and shows a diseased condition.

FIG. 5(a) shows the short axis scan state where the probe is perpendicular to the carotid artery; FIG. 5(b) shows the probe in rotation; and FIG. 5(c) shows the long axis scan state.

FIG. 6(a) is a schematic diagram of a carotid artery; and FIG. 6(b) is a schematic diagram of the probe.

FIG. 7(a) is a diagram in which the center in the lengthwise direction is aligned with the carotid artery; FIG. 7(b) is a diagram for illustrating an image from a transducer array 8; FIG. 7(c) is a diagram for illustrating an image from a transducer array 9; FIG. 7(d) is a diagram for illustrating an image from a transducer array 10; and FIG. 7(e) is a diagram for illustrating an angular position relationship display image.

FIG. 8(a) is a diagram of a state where the center in the lengthwise direction is displaced to the side of a probe origin 1a; FIG. 8(b) is a diagram for illustrating an image from a transducer array 8; FIG. 8(c) is a diagram for illustrating an image from a transducer array 9; FIG. 8(d) is a diagram for illustrating an image from a transducer array 10; and FIG. 8(e) is a diagram for illustrating an angular position relationship display image.

FIG. 9(a) is a diagram of a state where the center in the lengthwise direction is displaced to the opposite side of the probe origin 1a; FIG. 9(b) is a diagram for illustrating an image from a transducer array 8; FIG. 9(c) is a diagram for illustrating an image from a transducer array 9; FIG. 9(d) is a diagram for illustrating an image from a transducer array 10; and FIG. 9(e) is a diagram for illustrating an angular position relationship display image.

FIG. 10(a) is a diagram for illustrating a positional relationship between a carotid artery 6 and transducer arrays in the course of rotation; FIG. 10(b) is a diagram for illustrating an image from a transducer array 8; FIG. 10(c) is a diagram for illustrating an image from a transducer array 9;

FIG. 10(d) is a diagram for illustrating an image from a transducer array 10; and FIG. 10(e) is a diagram for illustrating an angular position relationship image.

FIG. 11(a) is a diagram for illustrating a positional relationship between a carotid artery 6 and transducer arrays immediately before the end of rotation; FIG. 11(b) is a diagram for illustrating an image from a transducer array 8; FIG. 11(c) is a diagram for illustrating an image from a transducer array 9; FIG. 11(d) is a diagram for illustrating an image from a transducer array 10; and FIG. 11(e) is a diagram for illustrating an angular position relationship image.

FIG. 12(a) is a diagram for illustrating a positional relationship when the carotid artery 6 and the long axis of the transducer array 9 are aligned; FIG. 12(b) is a diagram for illustrating an image from a transducer array 8; FIG. 12(c) is a diagram for illustrating an image from a transducer array 9; FIG. 12(d) is a diagram for illustrating an image from a transducer array 10; and FIG. 12(e) is a diagram for illustrating an angular position relationship image.

FIG. 13(a) is a diagram for illustrating a positional relationship when the probe is over-rotated; FIG. 13(b) is a diagram for illustrating an image from a transducer array 8; FIG. 13(c) is a diagram for illustrating an image from a transducer array 9; FIG. 13(d) is a diagram for illustrating an image from a transducer array 10; and FIG. 13(e) is a diagram for illustrating an angular position relationship image.

FIG. 14(a) is a diagram for illustrating a positional relationship when the carotid artery 6 and the long axis of the transducer array 9 are in parallel but displaced sideways; FIG. 14(b) is a diagram for illustrating an image from a transducer array 8; FIG. 14(c) is a diagram for illustrating an image from a transducer array 9; FIG. 14(d) is a diagram for illustrating an image from a transducer array 10; and FIG. 14(e) is a diagram for illustrating an angular position relationship image.

DESCRIPTION OF EMBODIMENTS

The present invention will now be described in detail. However, the detailed description below and attached drawings are not intended to limit the present invention.

The present invention attains main objects with an arrangement comprising a controller to which a probe and a display are connected, wherein the controller causes the display to display a detected image of a target object detected by the probe and an angular position relationship image showing a relative angular position of the probe to the detected image of the target object.

As described above, the present invention provides an arrangement comprising a controller to which a probe and a display are connected, wherein the controller causes the display to display a detected image of a target object detected by the probe and an angular position relationship image showing a relative angular position of the probe to the detected image of the target object. Therefore, even a non-expert can take accurate measurements.

According to the present invention, the controller can cause the display to display a detected image of a target object detected by the probe and an angular position relationship image showing a relative angular position of the probe to the target object. Therefore, the probe can be placed correctly with respect to the target object while the operator is viewing the images displayed on the display, and as a result, even a non-expert can take accurate measurements.

Embodiments of the present invention will now be described below with reference to appended drawings.

(Embodiment 1)

Figure 1:
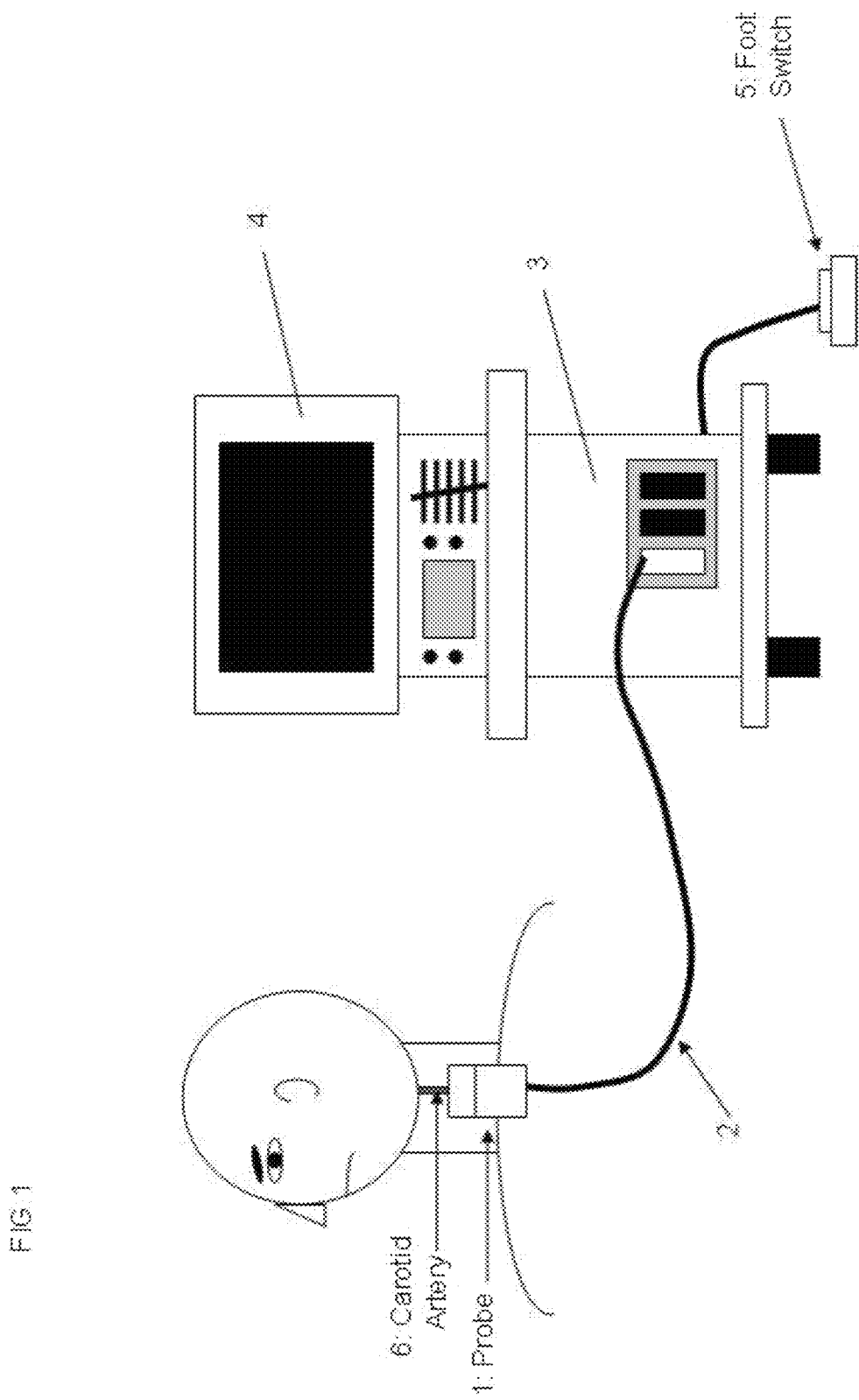
FIG. 1 is a diagram for illustrating an ultrasonograph of Embodiment 1 according to the present invention.

FIG. 1 is a diagram for illustrating an ultrasonograph of Embodiment 1 according to the present invention. The ultrasonograph of the embodiment comprises a probe 1, a controller 3 with the probe 1 connected thereto by a cable 2, a display 4 connected to the controller 3, and a foot switch 5.

The controller 3 is configured to cause the display 4 to display a detected image of a carotid artery 6 (an exemplary target object of a subject) detected by the probe 1 and an angular position relationship image showing a relative angular position of the probe 1 to the carotid artery 6.

Figure 2:
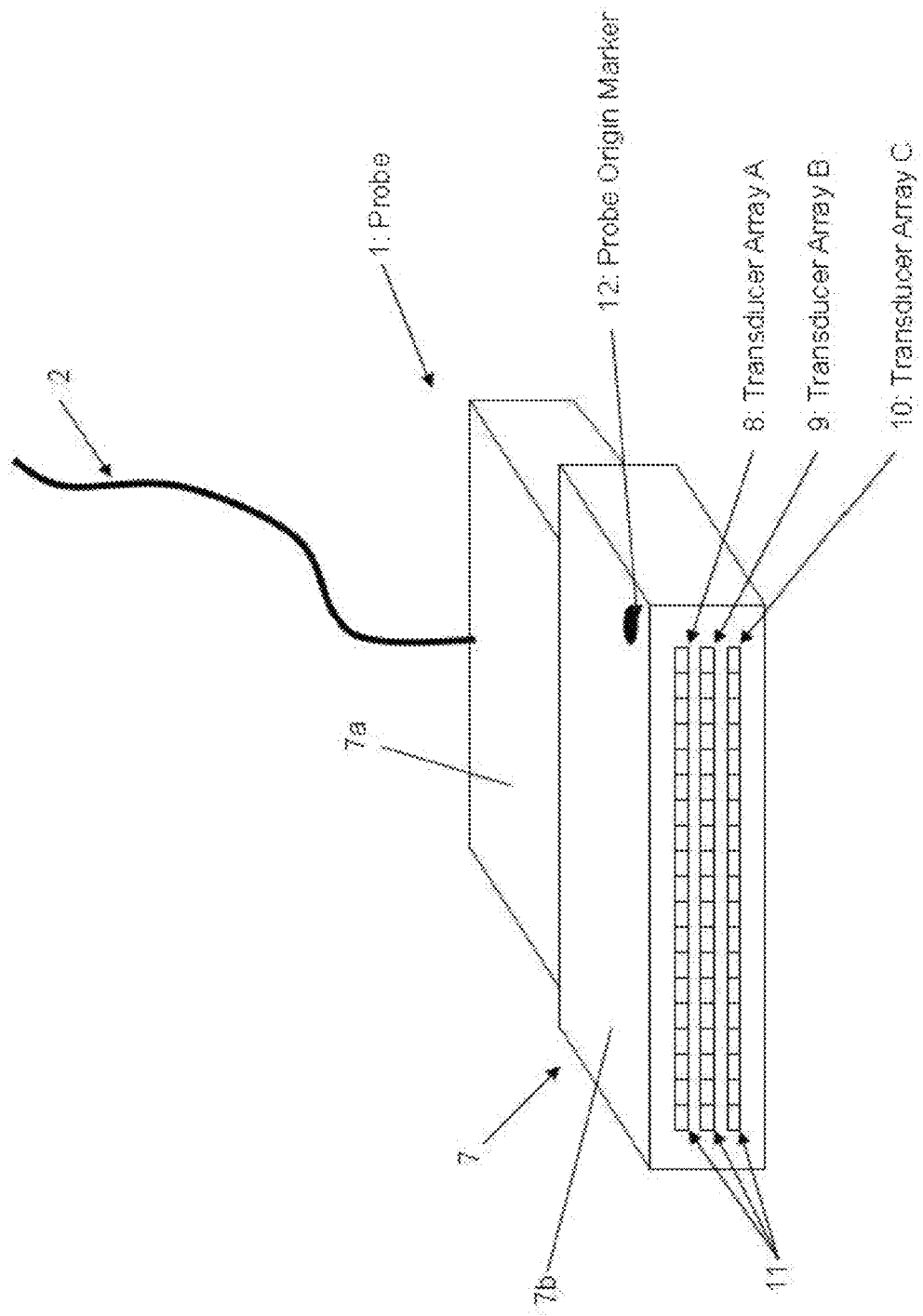
FIG. 2 is a perspective view showing a probe of the ultrasonograph of Embodiment 1 according to the present invention.

The probe 1 is composed of a number of (for example, three) transducer arrays 8 to 10 arranged in parallel to each other on the front side (or the side of a contact section with the subject) of a body casing 7, as shown in FIG. 2.

The probe 1 is also provided with a grip section 7a of a smaller diameter on an area of the cable 2 side of the body casing 7. The probe 1 is also provided with a contact section 7b that is oblong and has a larger diameter on an area opposite from the cable 2.

As shown in FIG. 2, a number of transducer arrays 8 to 10 extend in the lengthwise direction of the front surface (contact surface) of the contact section 7b. These extending transducer arrays 8 to 10 are spaced in parallel to each other.

Each of these transducer arrays 8 to 10 is composed of a number of ultrasonic transducers 11 arranged in line. As is well known, each of these transducer arrays 8 to 10 is arranged to obtain a wide detected image by sequentially switching a number of ultrasonic transducers 11 to change focus positions while the transducers are being driven.

Further, the transducer arrays 8 to 10 thus arranged in parallel to each other can provide a detected image of a strip-shaped area having a width.

As shown in FIG. 2, the probe 1 is also provided with a probe origin marker 12 on the top of the contact section 7b of the body casing 7 on one end side of the transducer arrays 8 to 10. As described below, the operator refers to the position of the probe origin marker 12 to adjust the position the probe 1.

Figure 3:
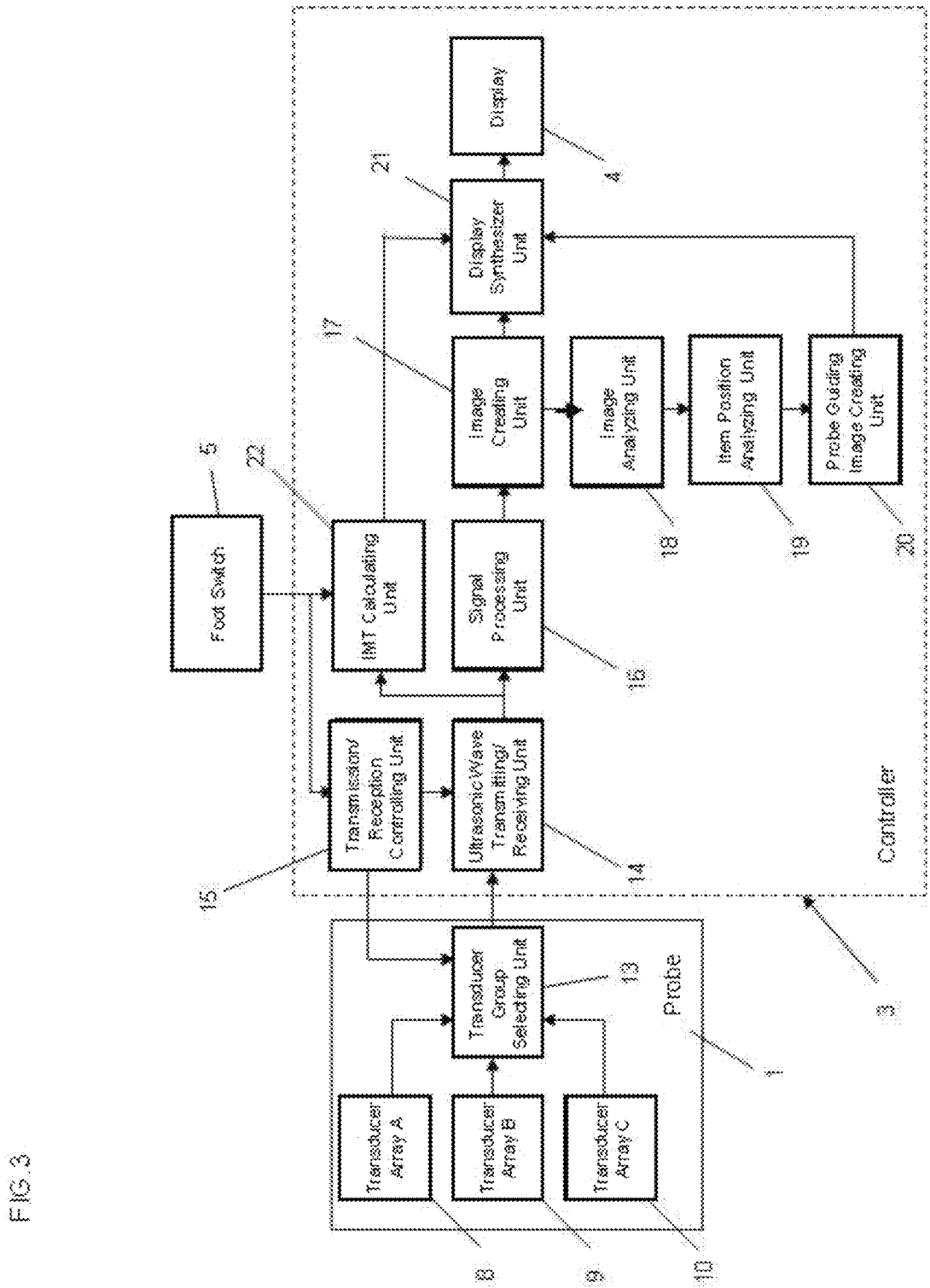
FIG. 3 is a control block diagram of the ultrasonograph of Embodiment 1 according to the present invention.

FIG. 3 is an electrical block diagram of the ultrasonograph. As shown in FIG. 3, a transducer group selecting unit 13 is connected to the transducer arrays 8 to 10 of the probe 1.

An electrical signal sent from an ultrasonic wave transmitting/receiving unit 14 of the controller 3 causes the transducer group selecting unit 13 to sequentially switch a number of ultrasonic transducers 11 to drive the transducers on each transducer array 8 to 10 basis.

With the electrical signal is applied, the ultrasonic transducers 11 of the transducer arrays 8 to 10 radiate ultrasonic waves toward the carotid artery 6 portion. Reflected waves from the carotid artery 6 portion are received by the ultrasonic transducers 11 that have previously radiated ultrasonic waves and converted to an electrical signal by the ultrasonic transducers 11.

The converted electrical signal is then sent to the ultrasonic wave transmitting/receiving unit 14 through the transducer group selecting unit 13. The sequence of control is performed in a transmission/reception controlling unit 15. The signal sent to the ultrasonic wave transmitting/receiving unit 14 is then processed in a signal processing unit 16. Thereafter, an image signal is generated in an image creating unit 17.

The image signal generated in the image creating unit 17 is then processed in an image analyzing unit 18, an item position analyzing unit 19, and a probe guiding image creating unit 20, in this order, and is sent to a display synthesizer unit 21.

The display synthesizer unit 21 has been supplied with an image signal generated in the image creating unit 17. Therefore, a probe guiding image generated in the probe guiding image creating unit 20 is superimposed on the image signal generated in the image creating unit 17, as described below.

The display synthesizer unit 21 is also adapted to be supplied with data calculated in an IMT CALCULATING unit 22. Therefore, the data is also superimposed on the image signal generated in the image creating unit 17 as visual information.

Figure 4:
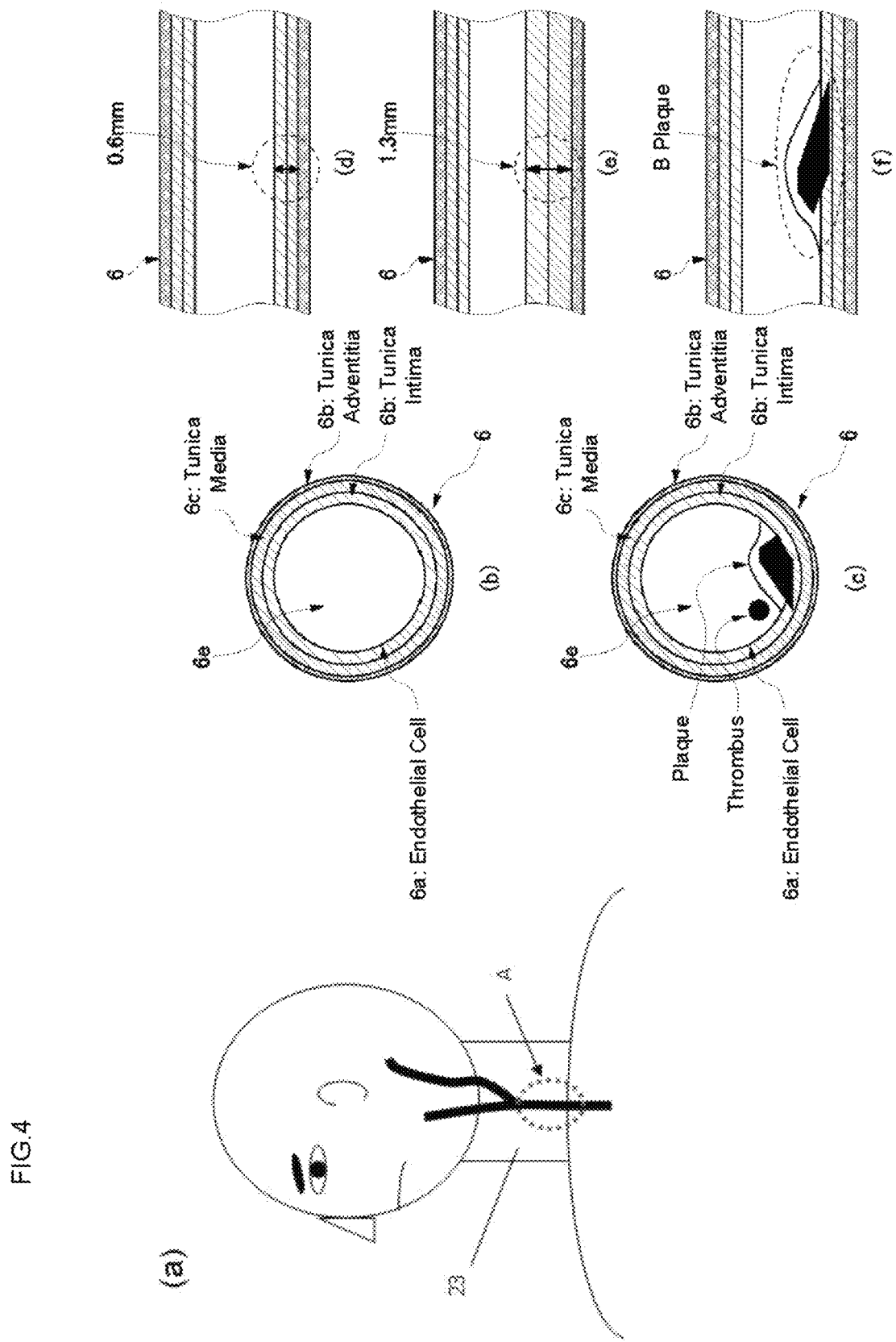
FIG. 4 are diagrams of cross sections of a carotid artery for illustrating an operation of the ultrasonograph.

FIG. 4(*a*) is a diagram showing a carotid artery 6 (target object (region A)) portion of a human body (subject) 23. After images in FIGS. 6 to 13, which will be described below, are displayed, any image in FIGS. 4(*d*) to 4(*f*) is displayed on the display 4. FIGS. 4(*d*) to 4(*f*) show detected images of the carotid artery 6 bisected longitudinally at a plane including the center line of the carotid artery. FIG. 4(*d*) is an image showing no particular condition, FIG. 4(*e*) is an image showing a condition where careful watching is needed, and FIG. 4(*f*) is an image showing a diseased condition.

These conditions will be described with reference to FIG. 4(*b*). As shown in FIG. 4(*b*), the carotid artery 6 is composed of an endothelial cell 6*a*, a tunica intima 6*b*, a tunica media 6*c*, and a tunica adventitia 6*d*, from the inside to the outside.

In the case of FIG. 4(*b*), since neither endothelial cell 6*a*, tunica intima 6*b*, nor tunica media 6*c* is raised toward a blood flowing area 6*e*, a large opening area of the blood flowing area 6*e* is observed. Therefore, the condition of FIG. 4(*b*) is normal, showing no particular condition. On the other hand, in the case of FIG. 4(*c*), since the endothelial cell 6*a*, the tunica intima 6*b*, and the tunica media 6*c* are raised toward a blood flowing area 6*e* due to plaque development (region B), the opening area of the blood flowing area 6*e* is reduced. Therefore, FIG. 4(*c*) shows a diseased condition.

FIG. 4(*d*) is an image showing no particular condition. In FIG. 4(*d*), as an example, data calculated in the IMT CALCULATING unit 22 in FIG. 3 is displayed as 0.6 mm. Similarly, it is displayed as 1.3 mm in FIG. 4(*e*). In FIG. 4(*f*), the displayed image shows a much higher level due to plaque development.

Both of the value 0.6 mm in FIG. 4(*d*) and the value 1.3 mm in FIG. 4(*e*) are referred to as an IMT value (a value of combined thickness of the endothelial cell 6*a* and the tunica media 6*c*). Since the case where the IMT value is at or above 1.1 mm is defined as a diseased condition according to the criteria of The Japan Academy of Neurosonology, it is determined that FIG. 4(*d*) shows no particular condition, FIG. 4(*e*) shows a condition where careful watching is needed, and FIG. 4(*f*) shows a diseased condition, as described above.

The facts shown in FIG. 4 are well known and further description will be omitted. In order to acquired such detected images as shown in FIGS. 4(*d*) to 4(*f*) with the conventional art, however, a fully trained expert must operate the probe 1.

Figure 5:
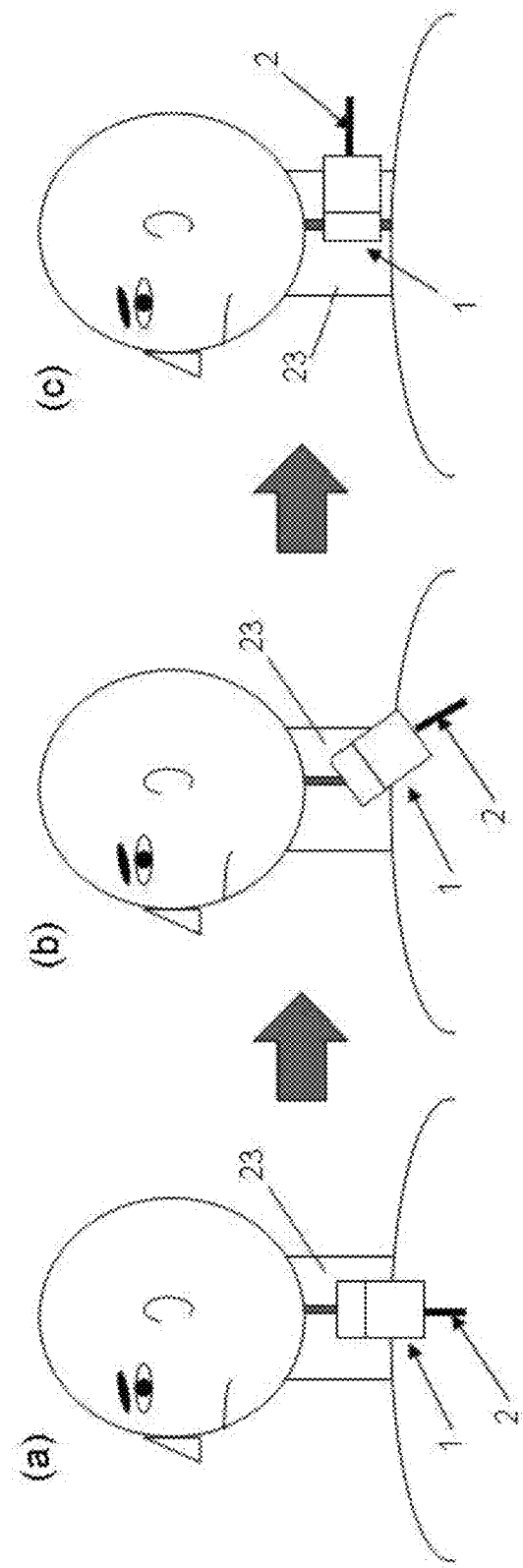
FIG. 5 are diagrams for illustrating a rotating operation of the probe from the short axis scan to the long axis scan of the carotid artery.

In contrast, according to the ultrasonograph of the embodiment, even a non-expert can merely operate the probe as shown in FIGS. 5(*a*) to 5(*c*) to easily acquire detected images as shown in FIGS. 4(*d*) to 4(*f*). In the operation in FIG. 5(*a*), the operator first presses the probe 1 against a neck 23 with the lengthwise direction of the transducer arrays 8 to 10 of the probe 1 (see FIG. 2) being substantially perpendicular to the neck 23 (carotid artery 6). Essentially, the probe 1 is in the short axis scan state relative to the carotid artery 6.

At this time, the operator determines where the carotid artery 6 runs on the probe 1. From this state, as in the operation in FIG. 5(*b*), the operator slowly rotates the probe 1 in a plane substantially in parallel to the contact surface into an upright position such that the lengthwise direction is along the center line of the carotid artery.

In the operation in FIG. 5(*c*), the lengthwise direction of the carotid artery 6 is aligned with the lengthwise direction of the transducer arrays 8 to 10; the probe 1 is essentially rotated from the short axis scan state to the long axis scan state relative to the carotid artery 6. In this way, detected images of the longitudinally bisected carotid artery 6 as shown in FIGS. 4(*d*) to 4(*f*) can be acquired.

At this time, the display 4 displays angular position relationship images of the probe 1 generated in the probe guiding image creating unit 20, so that even a non-expert can align the probe 1 with appropriate positions of the carotid artery 6 based on the display.

Figure 6:
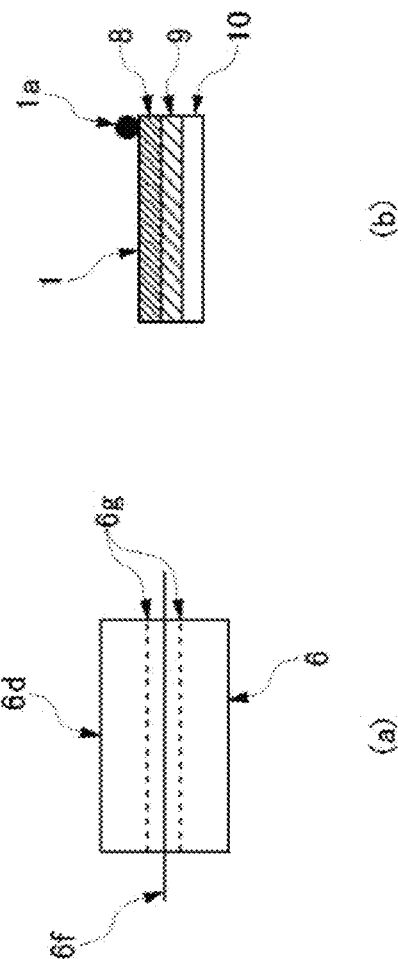
FIG. 6 are diagrams for illustrating a rotating operation of the probe from the short axis scan to the long axis scan of the carotid artery.

The sequence of operation will now be described with reference to FIGS. 6 to 14. FIG. 6(*a*) is a schematic view of the carotid artery 6. FIG. 6(*a*) shows a tunica adventitia 6*d*, the center axis 6*f* of the carotid artery 6, and detectable limits indicative of a detection range 6*g* on both sides of the center axis 6*f*.

FIG. 6(*b*) is a schematic view of the probe 1. As shown in FIG. 6(*b*), a probe origin 1*a* is located on one end side of the transducer arrays 8 to 10. The probe origin 1*a* is located on the same side as the probe origin marker 12 on the body casing 7 of the probe 1 (see FIG. 2).

Figure 7:
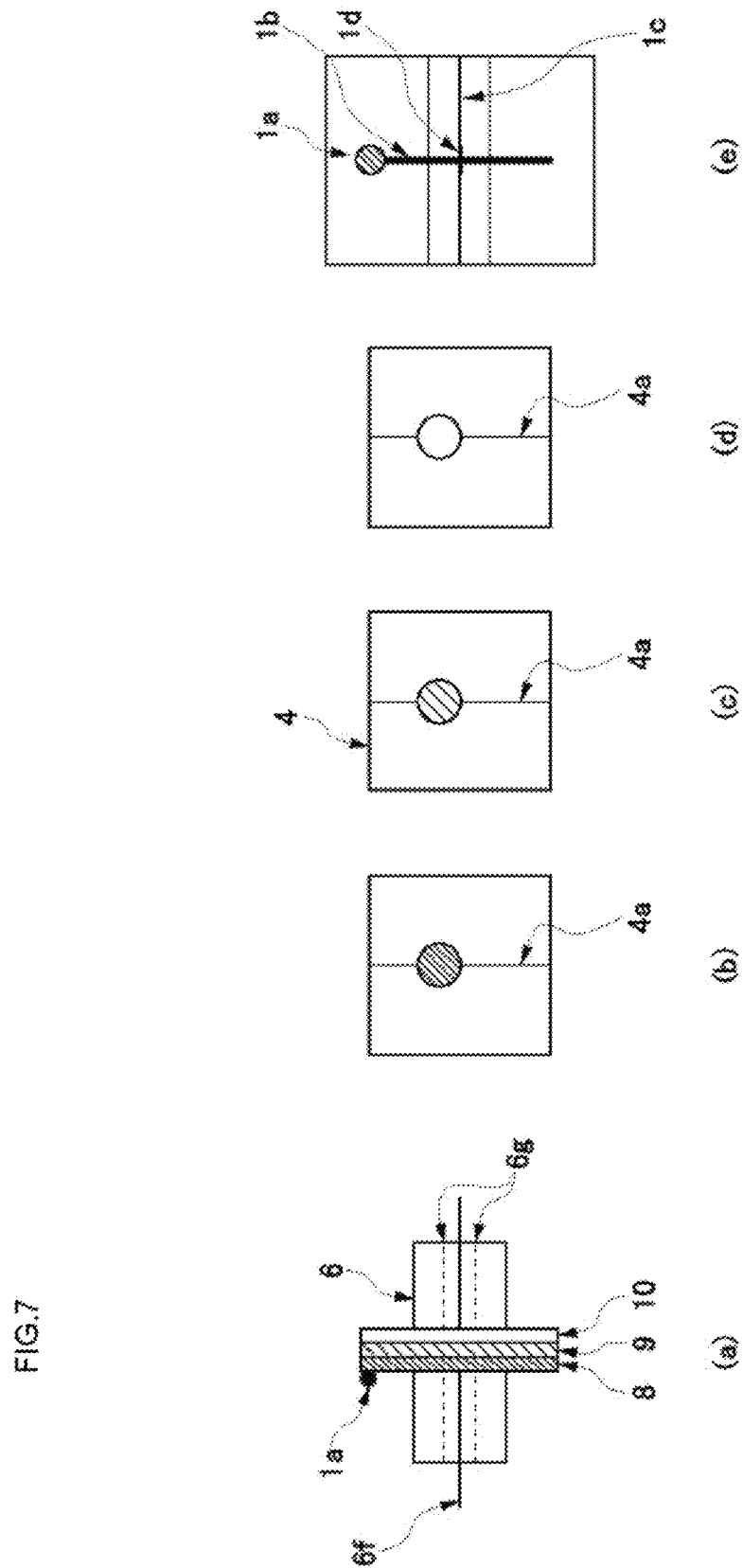
FIG. 7 are diagrams for illustrating a rotating operation of the probe from the short axis scan to the long axis scan of the carotid artery.
Figure 8:
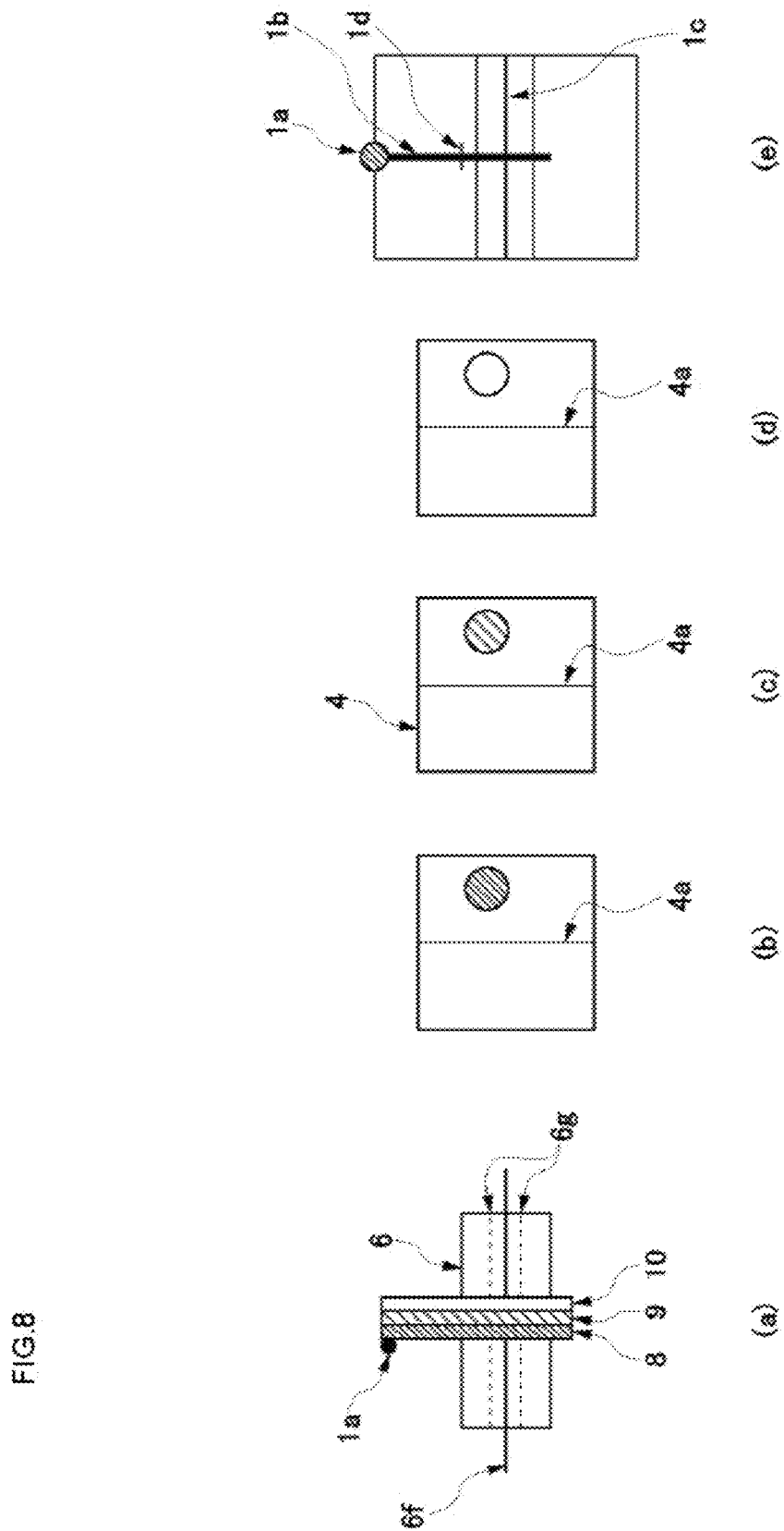
FIG. 8 are diagrams for illustrating a rotating operation of the probe from the short axis scan to the long axis scan of the carotid artery.
Figure 9:
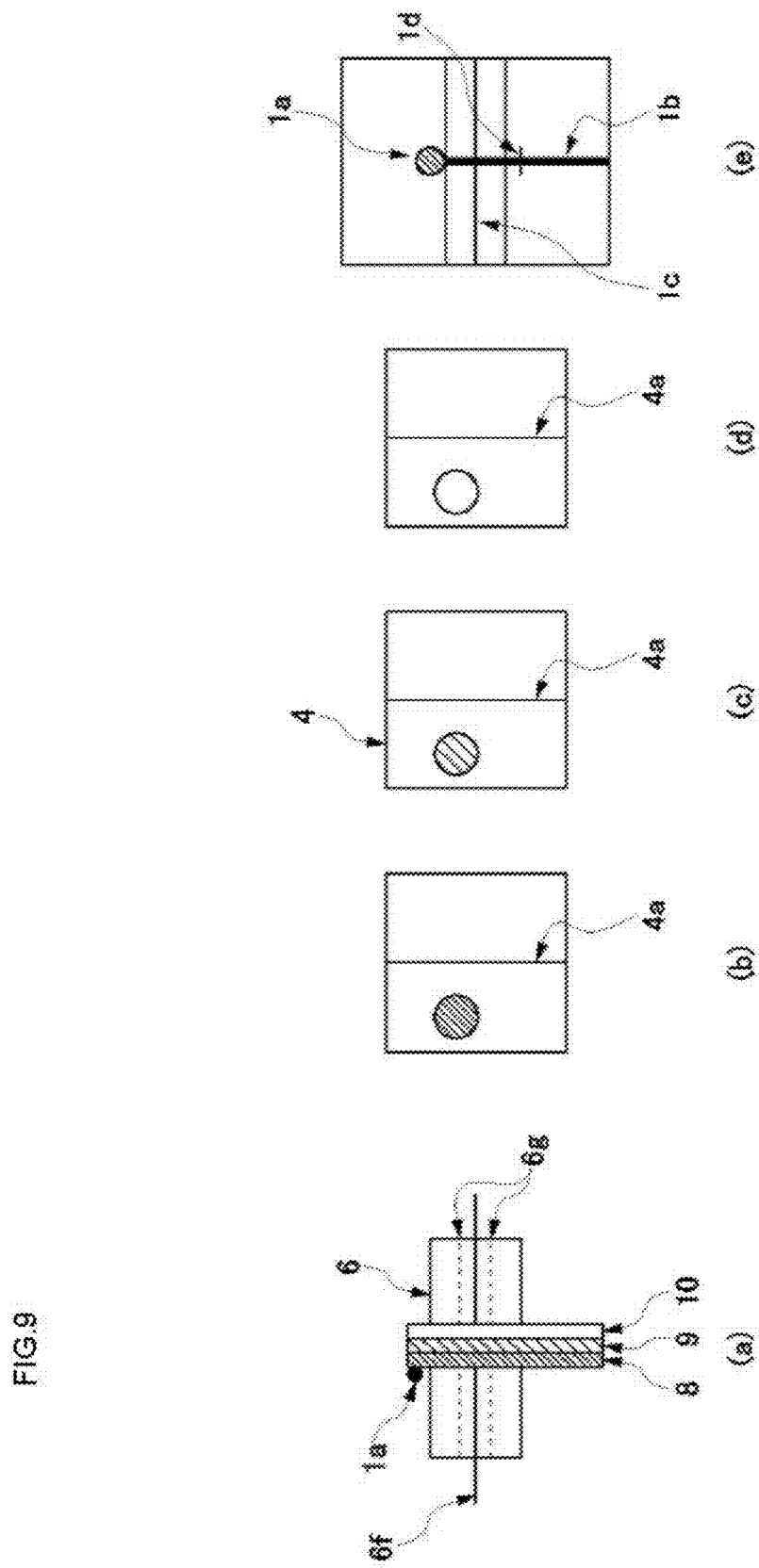
FIG. 9 are diagrams for illustrating a rotating operation of the probe from the short axis scan to the long axis scan of the carotid artery.

FIGS. 7 to 9 show display contents in association with the operation in FIG. 5(*a*). Specifically, FIGS. 7 to 9 show display contents for the display 4 when the probe 1 is pressed against the neck 23 with the lengthwise direction of the transducer arrays 8 to 10 of the probe 1 (see FIG. 2) being substantially perpendicular to the carotid artery 6.

FIG. 7(*a*) is a diagram of a state where the lengthwise direction of the transducer arrays 8 to 10 is substantially perpendicular in the center to the carotid artery 6 as in the operation in FIG. 5(*b*), and in any of the images from the transducer arrays 8 to 10 shown in FIGS. 7(*b*) to 7(*d*), horizontal sections of the carotid artery 6 that can be seen therein are located on the center line 4*a*.

Further, at this time, an angular position relationship image shown in FIGS. 7(*e*) also shows a state where a probe symbol 1*b* is perpendicular to a carotid center line symbol 1*c* and a middle point 1*d* of the probe symbol 1*b* is on the carotid center line symbol 1*c*.

The display 4 is now displaying the images in FIGS. 7(*c*) and 7(*e*). Specifically, the display 4 displays a large version of the image in FIG. 7(*c*) and a smaller angular position relationship image shown in FIG. 7(*e*) is displayed within a part of the image.

The image in FIGS. 7(*e*) is generated based on the images in FIGS. 7(*b*) to 7(*d*). Specifically, the images in FIGS. 7(*b*) and 7(*d*), as well as the image in FIG. 7(*c*), are analyzed in the image analyzing unit 18 and the item position analyzing unit 19 to determine what state the transducer arrays 8 to 10 of the probe 1 are placed in with respect to the carotid artery 6 based on positions, sizes, shapes, and the like of the three images, and the probe guiding image creating unit 20 generates an angular position relationship image as shown in FIG. 7(e). The angular position relationship image thus generated is displayed on the display 4.

The angular position relationship image shown in FIG. 7(e) constitutes a guiding screen (operation navigating information screen) for the probe 1. Watching the image in FIG. 7(e), the operator then rotate and move the probe 1.

For example, when the display in the display 4 is in the state shown in FIG. 7(e), the lengthwise direction of the transducer arrays 8 to 10 (the position indicated by the center line symbol 1c, which will be represented by 1c hereinafter) is perpendicular in the center to the carotid artery 6. At this time, in any of the images from the transducer arrays 8 to 10 shown in FIGS. 7(b) to 7(d), horizontal sections of the carotid artery 6 that can be seen therein are located on the center line 4a, as described above, and position adjustment for aligning the center of the transducer arrays 8 to 10 with the carotid artery 6 is completed.

In contrast, FIG. 8 show a state where the lengthwise direction of the probe 1 (or transducer arrays 8 to 10) is still perpendicular to the carotid artery 6, while the center 1c in the lengthwise direction of the probe 1 (or transducer arrays 8 to 10) is displaced to the side of a probe origin 1a (or the side of the probe origin marker 12 on the body casing 7) in the lengthwise direction of the probe 1 (or transducer arrays 8 to 10).

Further, FIG. 9 show a state where the lengthwise direction of the probe 1 is still perpendicular to the carotid artery 6, while the center in the lengthwise direction of the probe 1 (or transducer arrays 8 to 10) is displaced to the opposite side of a probe origin 1a (or the probe origin marker 12 on the body casing 7) of the probe 1. During operation in FIGS. 7 to 9, the images in FIGS. 7(c), 7(e), 8(c), 8(e), 9(c) and 9(e) are displayed on the display 4 as probe guiding images.

For example, when the images in FIG. 8 are displayed, the operator moves the probe 1 horizontally along the neck 23 so as to place the middle point 1d of the probe symbol 1b on the carotid center line symbol 1c, based on the positional relationship between the middle point 1d of the probe symbol 1b in FIG. 8(e) and the probe origin 1a (or the probe origin marker 12 on the body casing 7).

For example, when the images in FIG. 9 are displayed, the operator moves (in the direction opposite from that in FIG. 8) the probe 1 horizontally along the neck 23 so as to place the middle point 1d of the probe symbol 1b on the carotid center line symbol 1c, based on the positional relationship between the middle point 1d of the probe symbol 1b in FIG. 9(e) and the probe origin 1a (or the probe origin marker 12 on the body casing 7).

After the operator has made correction from the state shown in FIG. 8 or 9 to the state shown in FIG. 7, the operator rotates the probe 1 in a direction so as to align with the longitudinal direction of the carotid artery 6, as shown in FIG. 5(b).

As shown in FIG. 5(b), at a point where the probe is in rotation from the state shown in FIG. 5(a) to the state shown in FIG. 5(c), detected images of the carotid artery 6 are elliptical. In this case, only the image in FIG. 10(c) is displayed on the display 4 among the images in FIGS. 10(b) and 10(d).

Further in this case, the operation navigating information screen (angular position relationship image) shows a state where the probe symbol 1b is oblique with respect to the carotid center line symbol 1c, as shown in FIG. 10(e). At this time, the image in FIG. 10(e) is also generated based on the images in FIGS. 10(b) to 10(d). Specifically, the three images in FIGS. 10(b) to 10(d) are analyzed in the image analyzing unit 18 and the item position analyzing unit 19 to determine what state the transducer arrays 8 to 10 of the probe 1 are placed in with respect to the carotid artery 6 based on positions, sizes, shapes, and the like of the three images, and the probe guiding image creating unit 20 generates an angular position relationship image as shown in FIG. 10(e). The angular position relationship image thus generated is displayed on the display 4.

In this case, as shown in FIG. 10(e), while the middle point 1d of the probe symbol 1b intersects the carotid center line symbol 1c, the operator moves the probe 1 vertically along the neck 23 because the probe symbol 1b is largely oblique with respect to the carotid center line symbol 1c.

The angular position relationship image shown in FIG. 10(e) therefore constitutes a guiding screen for the probe 1. Watching the image in FIG. 10(e), the operator then rotates the probe 1. During the rotation, however, the middle point 1d of the probe symbol 1b still intersects the carotid center line symbol 1c.

During the rotation of the probe 1, if the middle point 1d of the probe symbol 1b is displaced and it no longer intersects the carotid center line symbol 1c, the operator first repositions the middle point 1d of the probe symbol 1b to intersect the carotid center line symbol 1c as a corrective operation.

During the corrective operation, the position of the probe origin 1a (or the probe origin marker 12 on the body casing 7) in the image on the display 4 may also be viewed for reference, which can be relied upon to restore the middle point 1d of the probe symbol 1b into the state where it intersects the carotid center line symbol 1c. The operator then rotates the probe 1 again from the state shown in FIG. 5(b) to the state shown in FIG. 5(c).

Figure 10:
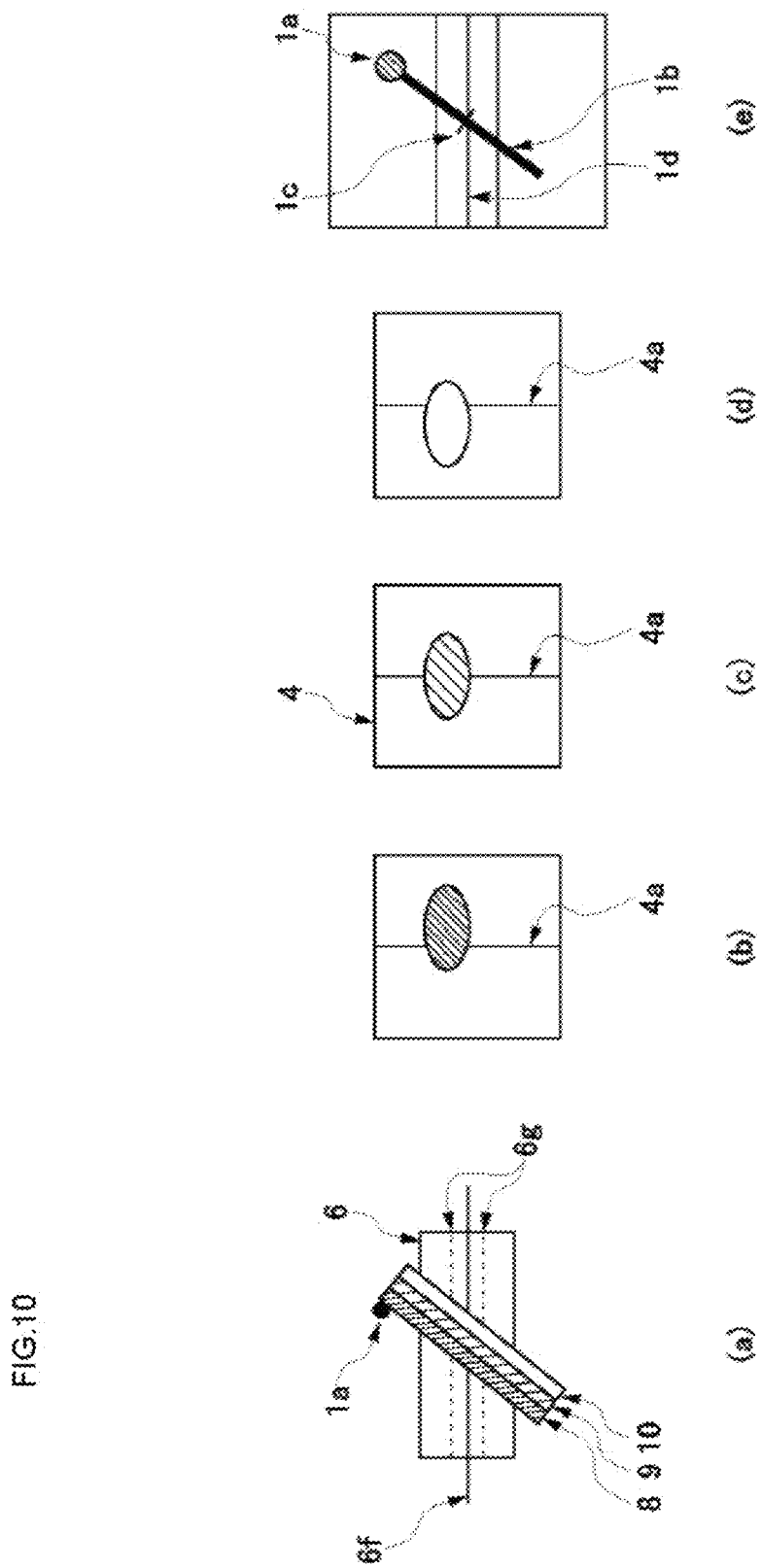
FIG. 10 are diagrams for illustrating a rotating operation of the probe from the short axis scan to the long axis scan of the carotid artery.
Figure 11:
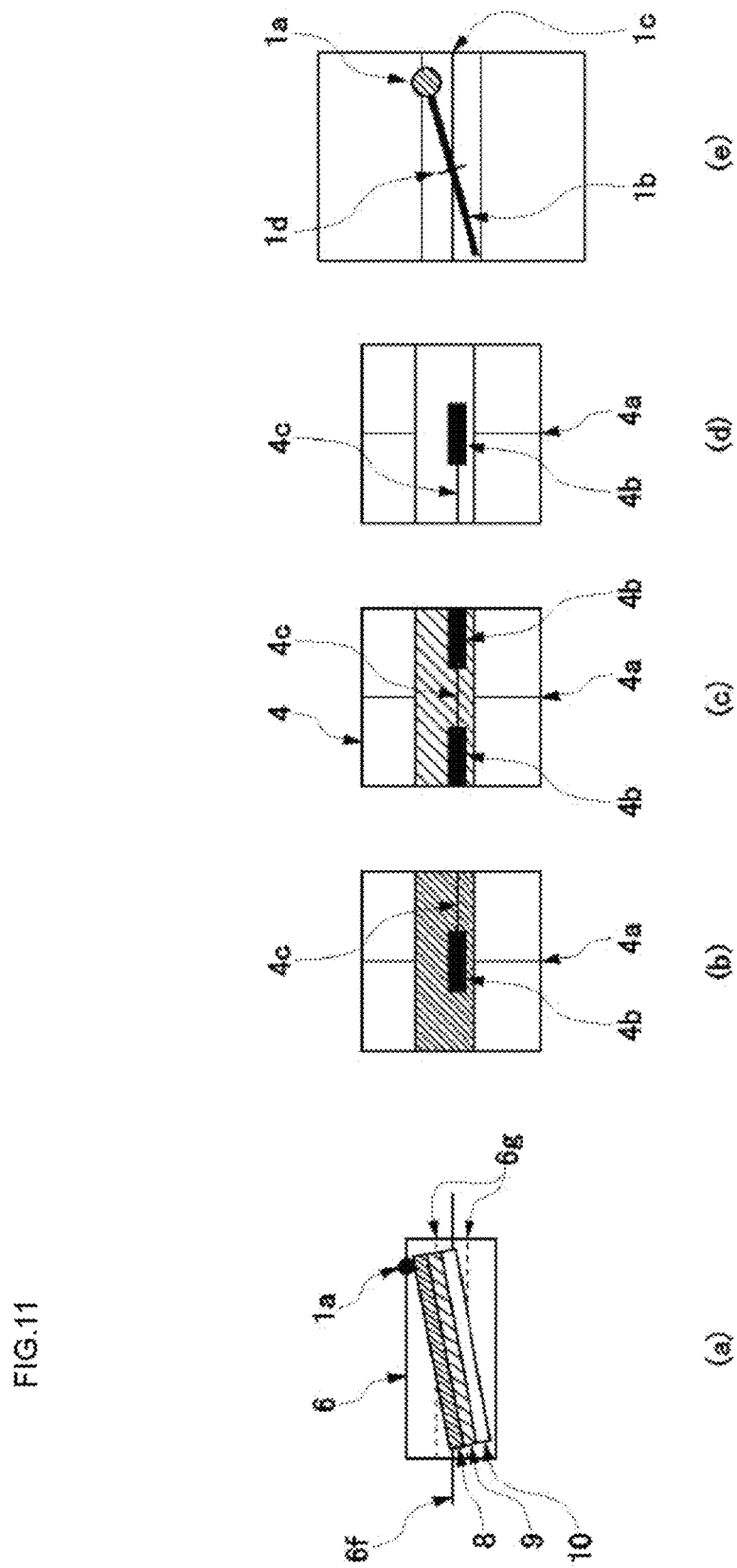
FIG. 11 are diagrams for illustrating a rotating operation of the probe from the short axis scan to the long axis scan of the carotid artery.

FIG. 11 show immediately before the final state during the rotation from the state shown in FIG. 5(b) to the state shown in FIG. 5(c). In this state, as shown in FIG. 11(a), the probe symbol 1b is closer to a horizontal state than the state shown in FIG. 10(e).

While the strip-shaped carotid artery 6 is emerging in FIG. 11(c), there are an unclear portion 4b and a clear portion 4c that is somewhat clearer than the unclear portion 4b in FIGS. 11(b) to 11(d). Therefore, an angular position relationship image in FIG. 11(e) is generated based on information of the unclear portions 4b in FIGS. 11(b) to 11(d).

Figure 12:
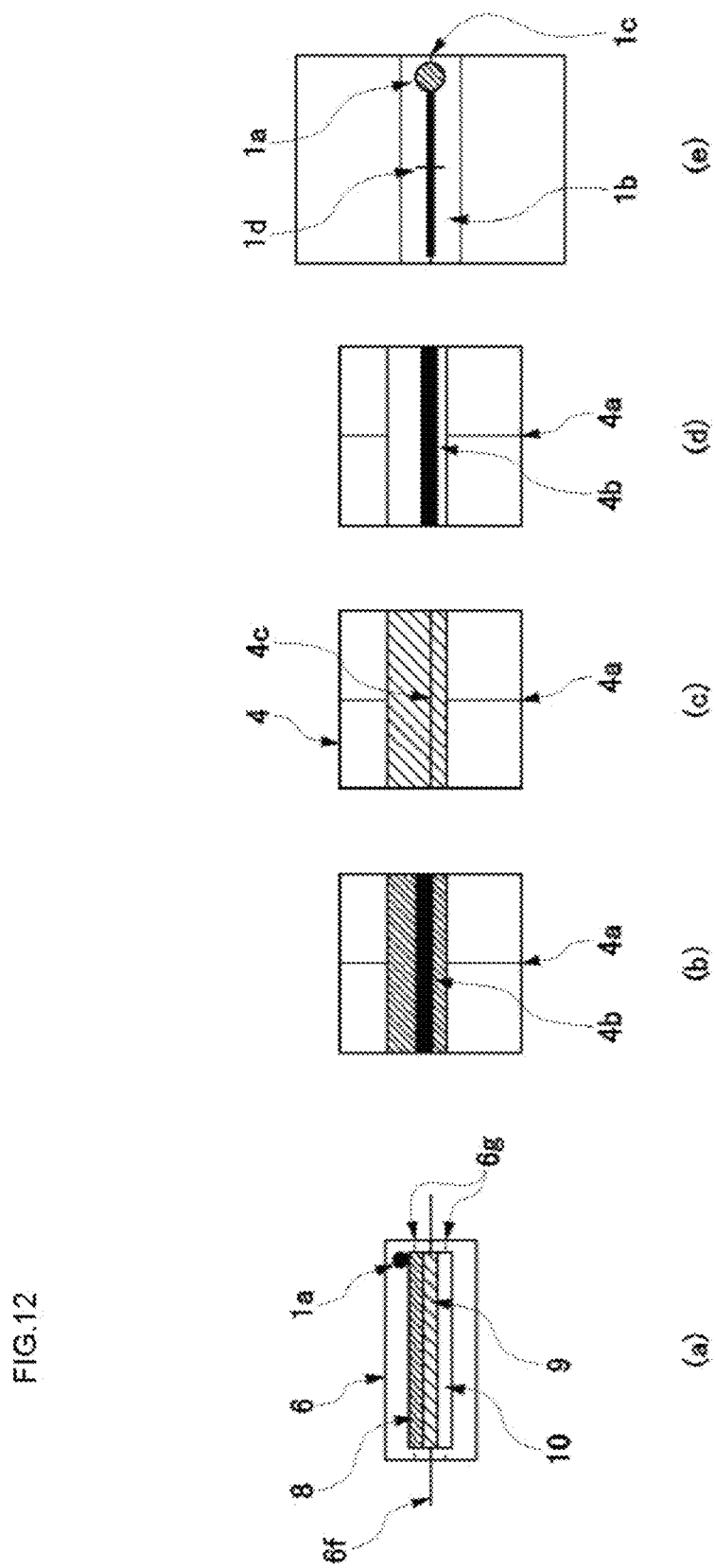
FIG. 12 are diagrams for illustrating a rotating operation of the probe from the short axis scan to the long axis scan of the carotid artery.

FIG. 12 show a state where the probe 1 is adjusted to a position bisecting a carotid artery 6 longitudinally along the center axis. In this case, as shown in FIG. 12(a), the probe symbol 1b coincides with the carotid center line symbol 1c. An angular position relationship image in FIG. 12(e) is generated based on clear appearance of the strip-shaped carotid artery 6 and the absence of any unclear portion 4b in FIG. 12(c) and the presence of unclear portions 4b in FIGS. 12(b) and 12(d).

Figure 13:
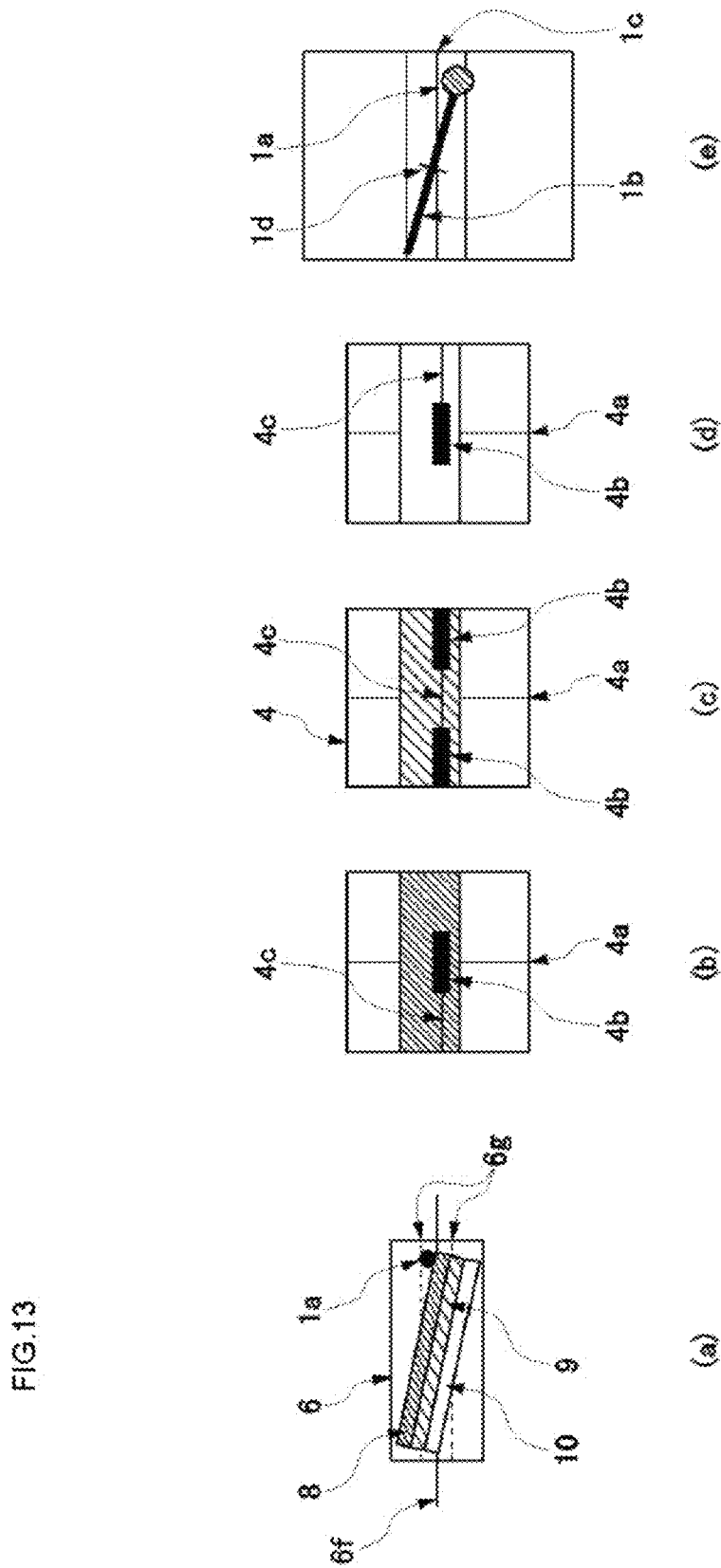
FIG. 13 are diagrams for illustrating a rotating operation of the probe from the short axis scan to the long axis scan of the carotid artery.

FIG. 13 show a state where the probe 1 passes over a position bisecting a carotid artery 6 longitudinally along the center axis and further over-rotated. In this case, as shown in FIG. 13(a), the probe symbol 1b is oblique with respect to the carotid center line symbol 1c toward the opposite side from that in FIG. 11(e). An angular position relationship image in FIG. 13(e) is generated based on appearance of the strip-shaped carotid artery 6 in FIG. 13(c) and the presence of unclear portions 4b in FIGS. 13(b) and 13(d), which also takes into consideration information indicative of difference in the position of the probe origin 1a from that in FIG. 11.

Figure 14:
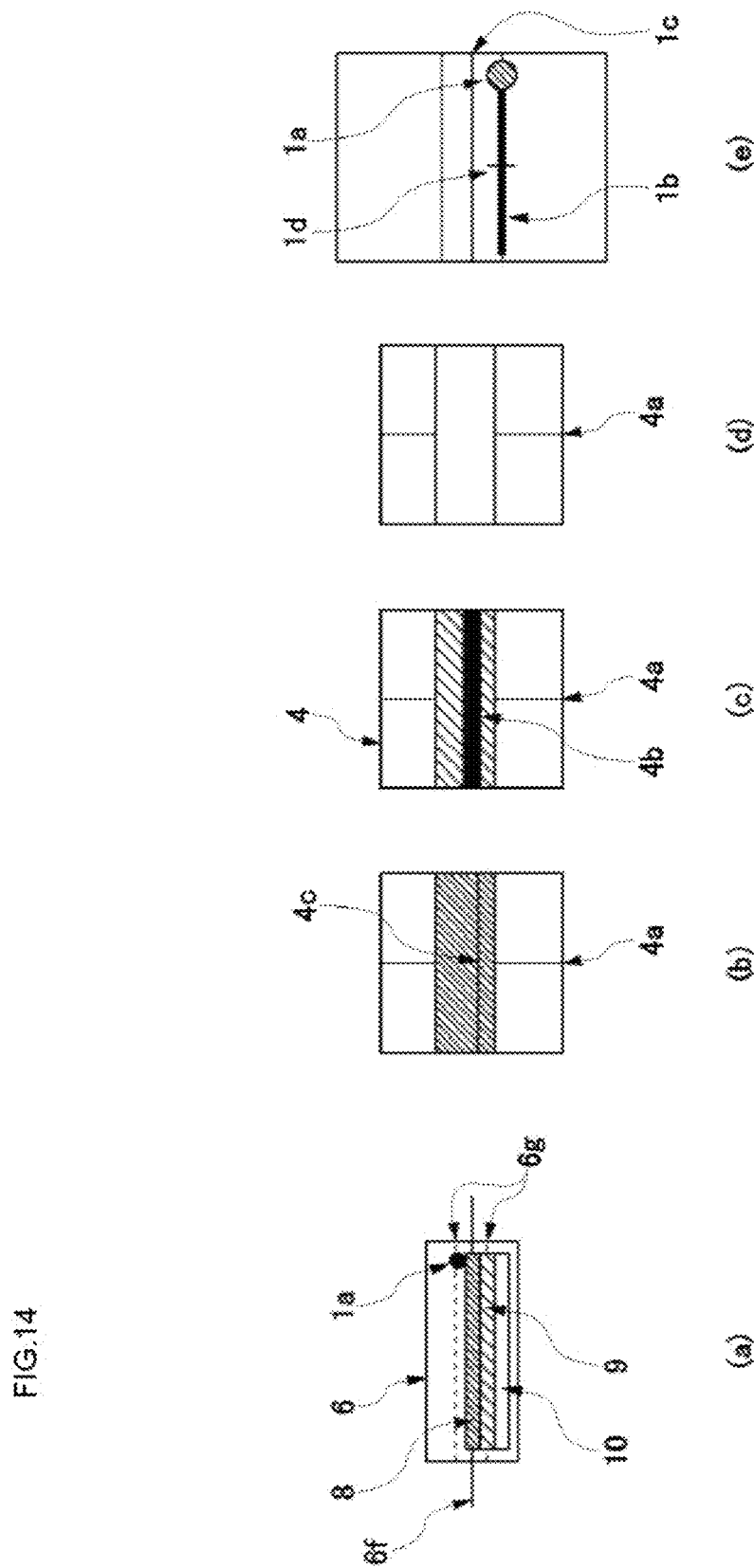
FIG. 14 are diagrams for illustrating a rotating operation of the probe from the short axis scan to the long axis scan of the carotid artery.

FIG. 14 show a state where the probe 1 passes over horizontally a position bisecting a carotid artery 6 longitudinally along the center axis (or a state where the probe 1 is displaced sideways (horizontally) in FIG. 5(c)). In this case, an angular position relationship image in FIG. 14(e) is generated based on appearance of the strip-shaped carotid artery 6, the presence of strip-shaped unclear portions 4b, and the like in FIG. 14(c).

As understood in the above description, according to the embodiment, the operator can easily move and adjust the probe 1 to an appropriate portion of the carotid artery 6 based on the angular position relationship images (those in FIGS. 7(e) to 14(e)) displayed on the display 4, which provides improved operability.

(Embodiment 2)

In Embodiment 1 described above, a number of transducer arrays 8 to 10 are used to acquire detected images of the carotid artery 6 as shown in FIG. 2. However, the probe 1 may be configured to move (swing) a single transducer array 9 (see FIG. 15) to left and right from the center so as to provide three pseudo-transducer arrays 8 to 10 in a similar way to FIG. 2.

In this case, displays in FIGS. 7 to 14 can be acquired from images at the center and images at the both sides from the center, which also allows the operator to easily move and adjust the probe 1 to an appropriate portion of the carotid artery 6, which provides improved operability.

Figure 15:
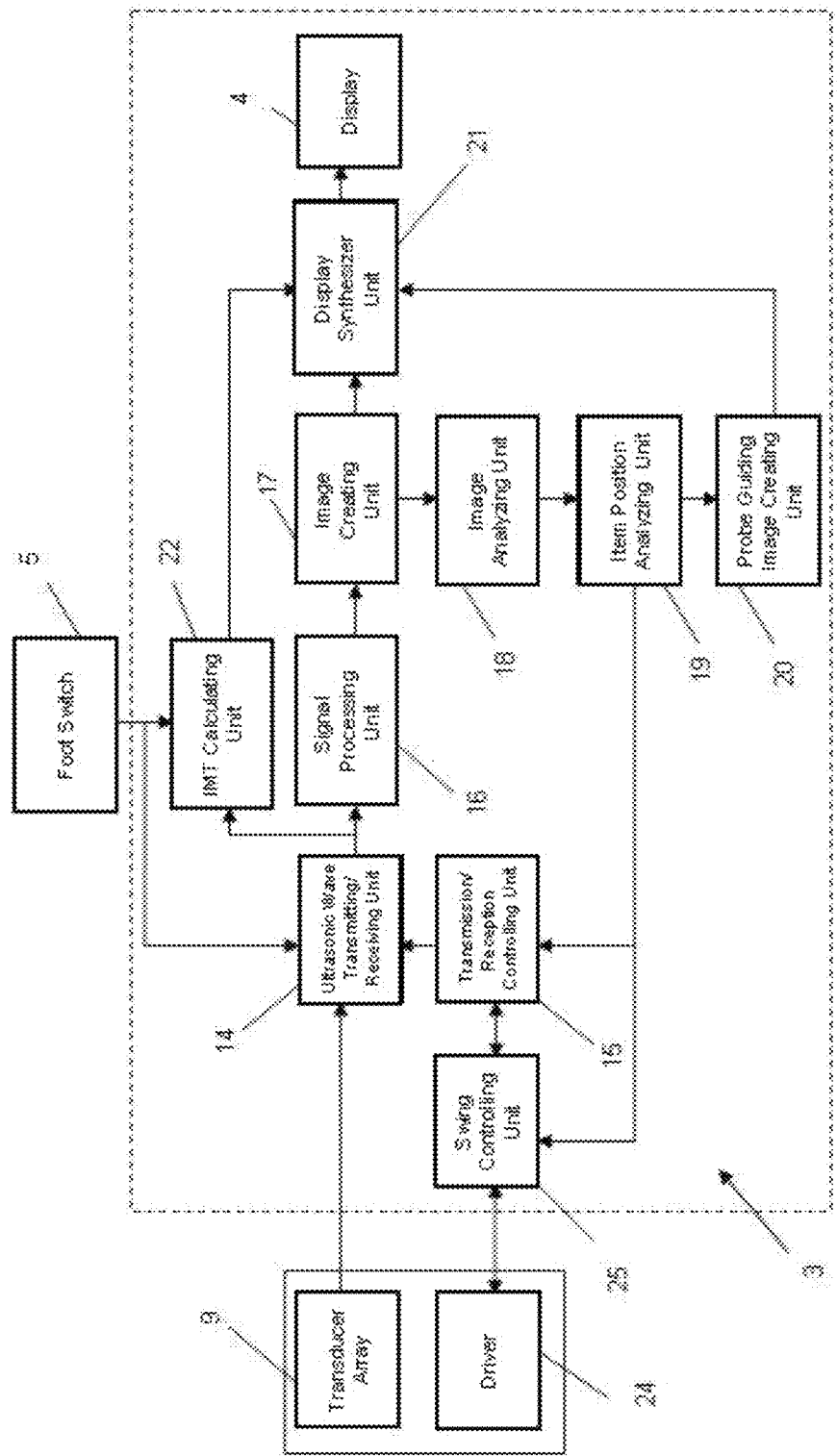
FIG. 15 is a block diagram of Embodiment 2 according to the present invention.

FIG. 15 is an electrical block diagram of an ultrasonograph according to the embodiment. In the ultrasonograph of the embodiment, the transducer array is provided with a Driver 24 for swinging the transducer array, and the Driver 24 is controlled by a swing controlling unit 25.

Depending on results of analysis by the item position analyzing unit 19, the range of left and right movement of the transducer array 9 may be varied. In this way, the amount of displacement of the carotid artery 6 such as shown in FIG. 10 can be increased, and as a result, the accuracy of analysis by the item position analyzing unit 19 can be improved.

(Embodiment 3)

In Embodiments 1 and 2 described above, a single display unit 4 is adapted to display a detected image of the carotid artery 6 simultaneously with an angular position relationship image that shows an angular position relationship between the probe 1 and the carotid artery 6 by using the display synthesizer unit 21, as shown in FIGS. 2 and 15. However, as shown in FIG. 16, the display unit 4 may be modified to have two or more display units (41 and 42) and each display unit may be configured to allow selection between displaying only the detected image of the carotid artery 6, displaying only the angular position relationship image that shows an angular position relationship between the probe 1 and the carotid artery 6, and displaying the detected image of the carotid artery 6 simultaneously with the angular position relationship image that shows an angular position relationship between the probe 1 and the carotid artery 6.

Figure 16:
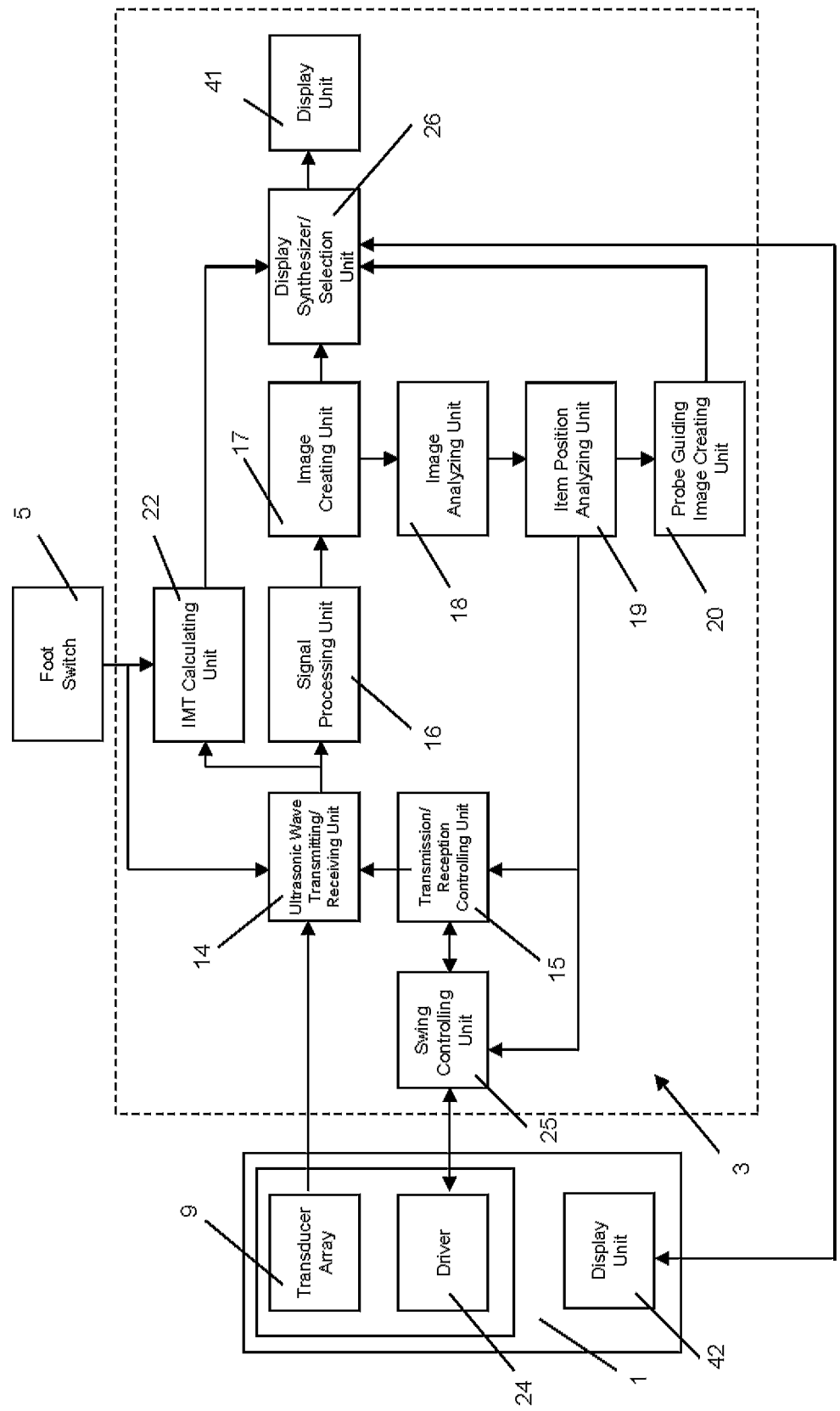
FIG. 16 is a block diagram of Embodiment 3 according to the present invention.

FIG. 16 is an electrical block diagram of an ultrasonograph according to the embodiment. The ultrasonograph of the embodiment is provided with a display synthesizer/selection unit 26 in place of the display synthesizer unit 21, and is configured to control two or more (two in the embodiment) display units 41 and 42 for display.

Here, the display synthesizer/selection unit 26 can control any of the display units and images independently in any combination thereof and cause the display units 41 and 42 to display only the detected image of the carotid artery 6, display only the angular position relationship image that shows an angular position relationship between the probe 1 and the carotid artery 6, or display the detected image of the carotid artery 6 simultaneously with the angular position relationship image that shows an angular position relationship between the probe 1 and the carotid artery 6.

With such a configuration, another display unit can be provided separately from a display unit provided in the ultrasonograph main unit. In the description below, the display unit provided in the ultrasonograph main unit is referred to as a display unit 41, and the other display unit provided separately from the display unit provided in the ultrasonograph main unit is referred to as a display 42.

In this case, the display unit 42 may be located near the probe 1 or incorporated into the probe 1. Therefore, when the probe 1 is used to search the position of center of the carotid artery 6, the operator can operate the probe 1 while the operator is viewing an angular position relationship image displayed on the display unit 42. Therefore, a forced unnatural posture and eye movement of the operator can be reduced as much as possible, which provides improved operability.

Although currently possible preferred embodiments of the invention have been described above, it is understood that various modifications can be made to the embodiments and it is intended that all such modifications that fall within the true spirit and scope of the invention are covered by the attached claims.

INDUSTRIAL APPLICABILITY

As described above, the present invention provides an arrangement comprising a controller to which a probe and a display are connected, wherein the controller causes the display to display a detected image of a target object detected by the probe and an angular position relationship image showing a relative angular position of the probe to the detected image of the target object. Therefore, even a non-expert can take accurate measurements. According to the present invention, the controller can cause the display to display a detected image of a target object detected by the probe and an angular position relationship image showing a relative angular position of the probe to the target object. Therefore, the operator can place the probe correctly with respect to the target object while the operator is viewing the images displayed on the display, and as a result, even a non-expert can take accurate measurements.

The ultrasonograph of the present invention is therefore expected to be widely utilized in examination of, for example, a carotid artery.

REFERENCE SIGNS LIST

1 Probe
1a Probe origin
1b Probe symbol
1c Carotid center line symbol
1d Middle point 1d
2 Cable
3 Controller
4 Display
4a Center line
4b Unclear portion
5 Foot switch
6 Carotid artery (an exemplary target object)
6a Endothelial cell
6b Tunica intima
6c Tunica media
6d Tunica adventitia
6e Blood flowing area
6f Center axis of carotid artery 6
6g Detection range
7 Body casing
7a Grip section 7b Contact section
8, 9, 10 Transducer array
11 Ultrasonic transducer
13 Transducer group selecting unit
14 Ultrasonic wave transmitting/receiving unit
15 Transmission/reception controlling unit
16 Signal processing unit
17 Image creating unit
18 Image analyzing unit
19 Item position analyzing unit
20 Probe guiding image creating unit
21 Display synthesizer unit
22 IMT CALCULATING unit
23 Neck
24 Driver
25 Swing controlling unit
26 Display synthesizer/selection unit
41 Display unit
42 Display unit

The invention claimed is:

1. An ultrasonograph comprising a controller to which a probe and a display are connected, wherein:
   based on an analysis on a detected image of a target object detected by the probe, the controller generates a positional relationship image showing a positional relationship between the probe and the target object, and causes the display to display the positional relationship image;
   the positional relationship image is displayed on a part of the detected image; and
   a center line of the target object and a probe symbol indicative of a positional state of the probe including obliqueness of the probe with respect to the center line are displayed in the positional relationship image.

2. The ultrasonograph according to claim 1, wherein a probe origin indicative of a position of origin of the probe is displayed in the positional relationship image.

3. The ultrasonograph according to claim 1, wherein detectable limits are displayed on both sides of the center line of the target object in the positional relationship image.

4. The ultrasonograph according to claim 1, wherein the probe is provided with a probe origin marker.

5. An ultrasonograph comprising a controller to which a probe and a display are connected, wherein:
   based on an analysis on a detected image of a target object detected by the probe, the controller generates a positional relationship image showing a positional relationship between the probe and the target object, and causes the display to display the positional relationship image;
   the probe is composed of a plurality of transducer arrays arranged in parallel to each other, and each of the plurality of transducer arrays is composed of a plurality of ultrasonic transducers arranged in line; and
   the display unit displays an image of the target object acquired by the plurality of transducer arrays as an image showing a positional relationship including obliqueness of the probe with respect to the target object.

6. An ultrasonograph comprising a controller to which a probe and a display are connected, wherein:
   based on an analysis on a detected image of a target object detected by the probe, the controller generates a positional relationship image showing a positional relationship between the probe and the target object, and causes the display to display the positional relationship image; and
   the probe is composed of a single transducer array movable to a plurality of parallel positions, and the transducer array is composed of a plurality of ultrasonic transducers arranged in line.

7. The ultrasonograph according to claim 6, wherein the display unit displays an image of the target object acquired by moving the single transducer array to the plurality of parallel positions as an image showing a relative angular position of the probe to the target object.

* * * * *